US010675057B2

(12) United States Patent
Krieger et al.

(10) Patent No.: US 10,675,057 B2
(45) Date of Patent: Jun. 9, 2020

(54) VARIABLE STIFFNESS CANNULAE AND ASSOCIATED DELIVERY SYSTEMS AND METHODS

(71) Applicant: Cook Medical Technologies LLC, Bloomington, IN (US)

(72) Inventors: Joshua Frye Krieger, Bloomington, IN (US); Melissa Lonn, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 717 days.

(21) Appl. No.: 15/139,889

(22) Filed: Apr. 27, 2016

(65) Prior Publication Data

US 2016/0317185 A1    Nov. 3, 2016

Related U.S. Application Data

(60) Provisional application No. 62/153,789, filed on Apr. 28, 2015.

(51) Int. Cl.
*A61B 17/34* (2006.01)
*A61M 25/00* (2006.01)
(Continued)

(52) U.S. Cl.
CPC .... *A61B 17/3468* (2013.01); *A61B 17/00234* (2013.01); *A61B 17/3421* (2013.01); *A61B 17/3423* (2013.01); *A61F 2/01* (2013.01); *A61M 25/0013* (2013.01); *A61M 25/0054* (2013.01); *A61M 25/0138* (2013.01);
(Continued)

(58) Field of Classification Search
CPC ............ A61B 17/3421; A61B 17/3423; A61B 17/3468; A61B 2017/00309; A61B 2017/00778; A61B 2017/00986; A61B 2017/3425; A61F 2/01; A61F 2/2427; A61F 2/95; A61F 2002/001; A61F 2250/0018;
(Continued)

(56) References Cited

U.S. PATENT DOCUMENTS 4,781,186 A   11/1988 Simpson et al.
5,053,004 A   10/1991 Markel et al.
(Continued)

FOREIGN PATENT DOCUMENTS

EP   0315290   5/1989
EP   0937481   8/1999
(Continued)

OTHER PUBLICATIONS

International Searching Authority, "International Preliminary Report on Patentability," for International Patent No. PCT/US2016/029661, dated Oct. 31, 2017, pp. 1 through 6.
(Continued)

*Primary Examiner* — Jocelin C Tanner
(74) *Attorney, Agent, or Firm* — Buchanan Van Tuinen LLC (57) ABSTRACT

The disclosure relates to cannulae, delivery systems, methods of making cannulae, and methods of making delivery systems. A cannula comprises an elongate tubular member having a circumferential wall extending between a proximal end and a distal end and defining an interior lumen. A pattern of openings arranged in an interrupted spiral extends circumferentially along the elongate tubular member.

20 Claims, 8 Drawing Sheets

(51) Int. Cl.
- *A61M 25/01* (2006.01)
- *A61B 17/00* (2006.01)
- *A61F 2/01* (2006.01)
- *A61F 2/95* (2013.01)
- *A61F 2/24* (2006.01)

(52) U.S. Cl.
CPC .............. *A61B 2017/00309* (2013.01); *A61B 2017/00778* (2013.01); *A61B 2017/00986* (2013.01); *A61B 2017/3425* (2013.01); *A61F 2/2427* (2013.01); *A61F 2/95* (2013.01); *A61F 2002/011* (2013.01); *A61F 2250/0018* (2013.01)

(58) Field of Classification Search
CPC .......... A61M 25/0013; A61M 25/0015; A61M 25/0054; A61M 25/0138
See application file for complete search history.

(56) References Cited

U.S. PATENT DOCUMENTS

| | | | |
|---|---|---|---|
| 5,195,962 A * | 3/1993 | Martin | ................ A61M 25/001 604/43 |
| 5,228,441 A | 7/1993 | Lundquist | |
| 5,284,128 A | 2/1994 | Hart | |
| 5,315,996 A | 5/1994 | Lundquist | |
| 5,322,064 A | 6/1994 | Lundquist | |
| 5,322,505 A | 6/1994 | Krause et al. | |
| 5,329,923 A | 7/1994 | Lundquist | |
| 5,425,723 A | 6/1995 | Wang | |
| 5,454,787 A | 10/1995 | Lundquist | |
| 5,460,187 A | 10/1995 | Daigle et al. | |
| 5,477,856 A | 12/1995 | Lundquist | |
| 5,507,766 A | 4/1996 | Kugo et al. | |
| 5,573,520 A | 11/1996 | Schwartz et al. | |
| 5,605,543 A | 2/1997 | Swanson | |
| 5,685,868 A | 11/1997 | Lundquist | |
| 5,741,429 A | 4/1998 | Donadio et al. | |
| 5,755,714 A | 5/1998 | Murphy-Chutorian | |
| 5,833,692 A | 11/1998 | Cesarini et al. | |
| 5,897,533 A | 4/1999 | Glickman | |
| 5,922,003 A | 7/1999 | Anctil et al. | |
| 6,059,769 A | 5/2000 | Lunn et al. | |
| 6,102,890 A | 8/2000 | Stivland et al. | |
| 6,146,373 A | 11/2000 | Cragg et al. | |
| 6,228,073 B1 | 5/2001 | Noon et al. | |
| 6,246,914 B1 | 6/2001 | de la Rama et al. | |
| 6,273,404 B1 | 8/2001 | Holman et al. | |
| 6,286,555 B1 | 9/2001 | Paulker et al. | |
| 6,350,253 B1 | 2/2002 | Deniega et al. | |
| 6,428,489 B1 | 8/2002 | Jacobsen et al. | |
| 6,611,720 B2 | 8/2003 | Hata et al. | |
| 6,623,491 B2 | 9/2003 | Thompson | |
| 6,652,508 B2 | 11/2003 | Griffin et al. | |
| 6,749,560 B1 | 6/2004 | Konstorum et al. | |
| 6,860,898 B2 | 3/2005 | Stack et al. | |
| 7,001,369 B2 | 2/2006 | Griffin | |
| 7,914,467 B2 | 3/2011 | Layman et al. | |
| 7,918,819 B2 | 4/2011 | Karmarkar et al. | |
| 7,989,042 B2 | 8/2011 | Obara et al. | |
| 8,007,434 B2 | 8/2011 | Olson | |
| 8,048,004 B2 | 11/2011 | Davis et al. | |
| 8,092,444 B2 | 1/2012 | Lentz et al. | |
| 8,105,246 B2 | 1/2012 | Voeller et al. | |
| 8,182,465 B2 | 5/2012 | Griffin et al. | |
| 8,257,279 B2 | 9/2012 | Davis et al. | |
| 8,262,563 B2 | 9/2012 | Bakos et al. | |
| 8,292,827 B2 | 10/2012 | Musbach | |
| 8,376,961 B2 | 2/2013 | Layman et al. | |
| 8,409,114 B2 | 4/2013 | Pains | |
| 8,636,716 B2 | 1/2014 | Griffin et al. | |
| 8,684,953 B2 | 4/2014 | Cabiri | |
| 8,728,010 B2 | 5/2014 | Hirshman | |
| 8,728,116 B1 | 5/2014 | Janardhan et al. | |
| 2004/0097880 A1 | 5/2004 | Schur | |
| 2005/0125053 A1 | 6/2005 | Yachia et al. | |
| 2006/0004346 A1 | 1/2006 | Begg | |
| 2006/0100687 A1 * | 5/2006 | Fahey | ........................ A61F 2/95 623/1.11 |
| 2006/0200047 A1 * | 9/2006 | Galdonik | .......... A61M 25/0138 600/585 |
| 2007/0112331 A1 | 5/2007 | Weber et al. | |
| 2007/0208405 A1 * | 9/2007 | Goodin | ..................... A61F 2/95 623/1.11 |
| 2008/0021347 A1 | 1/2008 | Jacobsen | |
| 2008/0021400 A1 | 1/2008 | Jacobsen et al. | |
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077085 A1 | 3/2008 | Eidenschink et al. | |
| 2008/0086047 A1 | 4/2008 | McDaniel et al. | |
| 2008/0097398 A1 * | 4/2008 | Mitelberg | ......... A61M 25/0043 604/525 |
| 2008/0294231 A1 | 11/2008 | Aguilar et al. | |
| 2009/0036832 A1 | 2/2009 | Skujins et al. | |
| 2009/0043228 A1 | 2/2009 | Northrop et al. | |
| 2009/0043283 A1 | 2/2009 | Turnlund et al. | |
| 2009/0043372 A1 | 2/2009 | Northrop et al. | |
| 2009/0177040 A1 | 7/2009 | Lyons et al. | |
| 2009/0192584 A1 | 7/2009 | Gerdts et al. | |
| 2010/0036364 A1 | 2/2010 | Wubbeling | |
| 2010/0063479 A1 * | 3/2010 | Merdan | ................ A61B 1/0011 604/528 |
| 2010/0069882 A1 | 3/2010 | Jennings et al. | |
| 2010/0145308 A1 | 6/2010 | Layman et al. | |
| 2011/0022069 A1 | 1/2011 | Mitusina | |
| 2011/0251519 A1 | 10/2011 | Romoscanu | |
| 2011/0276034 A1 | 11/2011 | Tomarelli et al. | |
| 2012/0053419 A1 | 3/2012 | Bloom | |
| 2012/0157935 A1 | 6/2012 | Wuebbeling et al. | |
| 2012/0265229 A1 | 10/2012 | Rottenberg et al. | |
| 2013/0046285 A1 | 2/2013 | Griffin et al. | |
| 2013/0072904 A1 | 3/2013 | Musbach et al. | |
| 2013/0123768 A1 * | 5/2013 | Harlan | .................. A61M 25/09 606/15 |
| 2013/0296718 A1 | 11/2013 | Ranganathan et al. | |
| 2013/0304035 A1 | 11/2013 | Cabiri | |
| 2014/0031843 A1 | 1/2014 | Rottenberg et al. | |
| 2014/0053940 A1 | 2/2014 | Konstorum et al. | |
| 2014/0121590 A1 | 5/2014 | Degen | |
| 2015/0297863 A1 * | 10/2015 | Hannon | ............ A61M 25/0009 604/544 |
| 2015/0342580 A1 | 12/2015 | Clancy | |

FOREIGN PATENT DOCUMENTS

| | | |
|---|---|---|
| EP | 1656963 | 11/2004 |
| EP | 1656963 | 5/2006 |
| EP | 1656963 A1 | 5/2006 |
| EP | 2364746 | 9/2011 |
| WO | WO199011313 | 3/1999 |
| WO | WO2002055146 | 7/2002 |
| WO | 2011/008538 A1 | 1/2011 |
| WO | 2011008538 | 1/2011 |
| WO | WO2011008538 | 1/2011 |
| WO | WO2016176393 | 11/2016 |

OTHER PUBLICATIONS

European Patent Office, Extended European Search Report for Application No. EP17178169, dated Nov. 13, 2017, p. 1 through 8.
International Searching Authority, International Search Report and Written Opinion for International Application No. PCT/US2016/029661, dated Jul. 27, 2016, p. 1-11.
European Patent Office, Communication pursuant to Rule 161(1) and 162 for Application No. 16721595.3, dated Dec. 6, 2017, pp. 1-2.

(56) References Cited

OTHER PUBLICATIONS

International Searching Authority, International Preliminary Report on Patentability for Application No. PCT/US2016/029661, dated Oct. 31, 2017, pp. 1-6.

* cited by examiner

VARIABLE STIFFNESS CANNULAE AND ASSOCIATED DELIVERY SYSTEMS AND METHODS

CROSS-REFERENCE TO RELATED APPLICATIONS

This application claims the benefit of U.S. Provisional Patent Application No. 62/153,789, filed Apr. 28, 2015, which is incorporated by reference into this disclosure in its entirety.

FIELD

The disclosure relates generally to the field of medical devices. More particularly, the disclosure relates to the fields of cannulae, delivery systems, and methods of making medical devices.

BACKGROUND

Delivery systems for implanting intraluminal medical devices at a point of treatment within a body vessel require both pushability and flexibility. Development of delivery systems and delivery system components that provide these desirable characteristics continues.

BRIEF SUMMARY OF SELECTED EXAMPLES

Several cannulae are described and illustrated herein. An example cannula comprises an elongate tubular member having a circumferential wall extending between a proximal end and a distal end and defining an interior lumen; a pattern of openings extends along a portion of the axial length of the cannula.

Another example cannula comprises an elongate tubular member having a circumferential wall extending between a proximal end and a distal end and defining an interior lumen; a pattern of openings extends along the entire axial length of the cannula.

Another example cannula comprises an elongate tubular member having a circumferential wall extending between a proximal end and a distal end and defining an interior lumen; a pattern of openings extends along an intermediate portion of the axial length of the cannula that is disposed between proximal and distal portions of the cannula that are free of the pattern of openings.

Another example cannula comprises an elongate tubular member having a circumferential wall extending between a proximal end and a distal end and defining an interior lumen; a pattern of openings extends along an intermediate portion of the axial length of the cannula that is disposed between proximal and distal portions of the cannula that are free of the pattern of openings; the proximal portion is longer than the distal portion.

Several delivery systems are described and illustrated herein. An example delivery system comprises a cannula comprising an elongate tubular member having a circumferential wall extending between a proximal end and a distal end and defining an interior lumen; a pattern of openings extending along an intermediate portion of the axial length of the cannula that is disposed between proximal and distal portions of the cannula that are free of the pattern of openings; the proximal portion is longer than the distal portion; an intraluminal medical device disposed on the distal portion of the cannula; and an elongate outer tubular member defining an outer tubular member lumen. The cannula is disposed within the outer tubular member lumen such that the intraluminal medical device is circumferentially disposed about the cannula and within the outer tubular member lumen.

Several methods of making a cannula are described and illustrated herein. An example method of making a cannula comprises identifying a cannula material and a cannula wall thickness that provides a desired global stiffness for said cannula; identifying one or more axial lengths of said cannula along which a localized stiffness, different from the desired global stiffness, is desired; identifying a pattern of openings that will provide the desired localized stiffness when cut into a cannula formed of the cannula material and having the cannula wall thickness; and cutting the pattern of openings into a cannula formed of the cannula material and having the cannula wall thickness at axial positions that correspond to the one or more axial lengths.

Several methods of making a delivery system are described and illustrated herein. An example method of making a delivery system comprises identifying a cannula material and a cannula wall thickness that provides a desired global stiffness for said cannula; identifying one or more axial lengths of said cannula along which a localized stiffness, different from the desired global stiffness, is desired; identifying a pattern of openings that will provide the desired localized stiffness when cut into a cannula formed of the cannula material and having the cannula wall thickness; cutting the pattern of openings into a cannula formed of the cannula material and having the cannula wall thickness at axial positions that correspond to the one or more axial lengths; disposing an intraluminal medical device on a portion of the cannula that is free of the pattern of openings; and inserting the cannula into an elongate tubular member defining a lumen such that the intraluminal medical device is circumferentially disposed about the cannula and within the lumen.

Additional understanding of the inventive cannulae, delivery systems and methods can be obtained by reviewing the description of selected examples, below, with reference to the appended drawings.

DETAILED DESCRIPTION OF SELECTED EXAMPLES

The following detailed description and appended drawings describe and illustrate various examples contemplated by the inventors. The description and drawings serve to enable one skilled in the art to make and use the inventive cannulae and delivery systems, and to practice the inventive methods; they are not intended to limit the scope of the invention or the protection sought in any manner. The invention is capable of being practiced or carried out in various ways; the examples described herein are merely selected examples of these various ways and are not exhaustive. As such, the language used in the description is to be given the broadest possible scope and meaning.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular.

Figure 1:
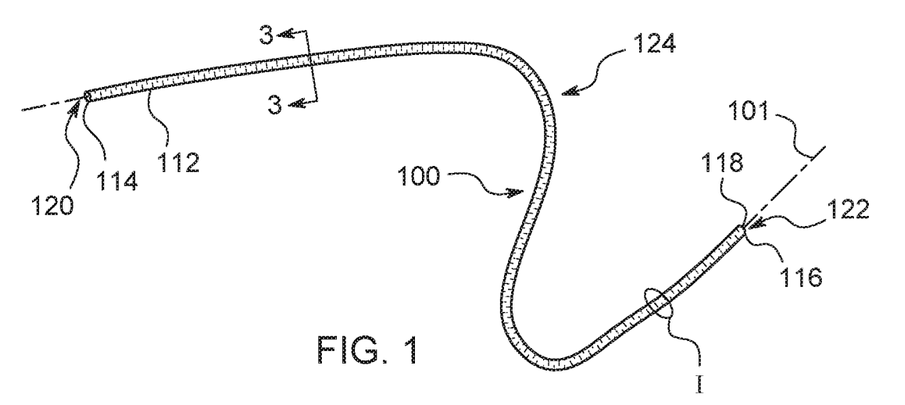
FIG. 1 is a perspective view of an example cannula.
Figure 2:
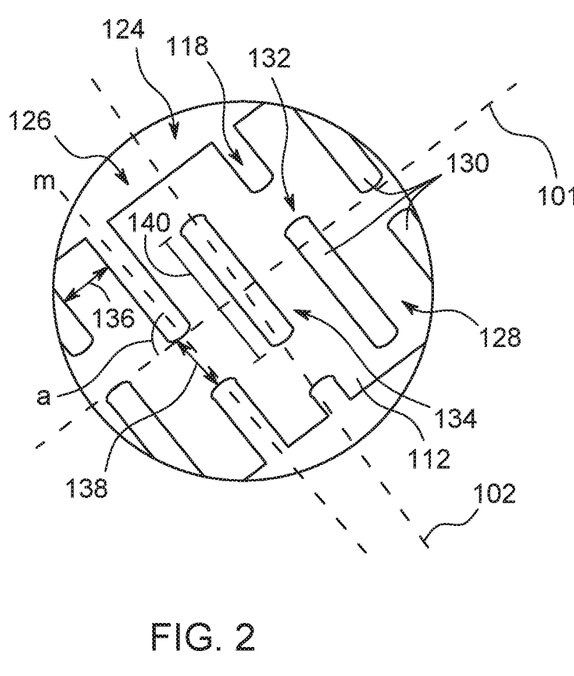
FIG. 2 is a magnified view of area I in FIG. 1.
Figure 3:
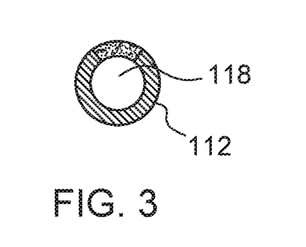
FIG. 3 is a magnified sectional view of the example cannula illustrated in FIG. 1, taken along line 3-3.

FIGS. 1, 2 and 3 illustrate a first example cannula 100. The cannula 100 is an elongate tubular member having a circumferential wall 112 extending between a proximal end 114 and a distal end 116. The circumferential wall 112 defines an interior lumen 118. A proximal opening 120 on the proximal end 114 provides access to the interior lumen 118. Similarly, a distal opening 122 on the distal end 116 provides access to the interior lumen 118. A longitudinal axis 101 extends centrally through the lumen. As best illustrated in FIG. 2, each of a plurality of transverse axes, such as transverse axis 102, lies on an individual plane that orthogonally intersects the longitudinal axis 101 at a point along its length.

A pattern of openings 124 extends along a portion of the axial length of the cannula 100. In the illustrated example, the pattern of openings 124 extends along the entire axial length of the cannula 100, extending between the proximal 114 and distal 116 ends. The pattern of openings 124 can extend along any suitable portion of the axial length of the cannula 100, though, and the entire axial length, as in the illustrated cannula 100, is only an example. For a cannula according to a particular example, a skilled artisan will be able to select a suitable portion of the axial length of the cannula along which the pattern of openings is to extend based on various considerations, including any need or desire for axial portions having a greater stiffness than that provided by an axial portion along which the pattern of openings extends. For example, if it is desirable to have an axial portion that has the global stiffness of the cannula material itself, the cannula can be made so that the pattern of openings does not extend along the axial portion for which the global stiffness is desired. Each of FIGS. 5, 6, and 7, described in detail below, illustrates an example cannula in which the pattern of openings does not extend along the entire axial length of the cannula.

As best illustrated in FIG. 2, the pattern of openings 124 comprises a plurality of openings 126 arranged in an interrupted spiral 128 that extends circumferentially along the circumferential wall 112 of the cannula 100. Each opening 130 of the plurality of openings 126 comprises an elongate slit that extends through the entire wall thickness of the circumferential wall 112 to provide access to the lumen 118 of the cannula 100. The elongate slit of each opening generally forms an oblong rectangle shape having a major axis m disposed on a plane that is transverse to the longitudinal axis 101 of the cannula 100. In the illustrated embodiment, one end 132 of the slit of each opening 130 has a slightly enlarged width, measured along the minor axis of the oblong rectangle of the slit. This enlarged width can be an artifact of some techniques used for forming the openings 130 in the circumferential wall 112 of the cannula 100, such as laser cutting. Inclusion of the enlarged width, accordingly, is considered optional. The overall pattern of openings 124 takes a spiral 128 configuration relative to the longitudinal axis of the cannula 100 because the major axis m of each opening is disposed on a plane that intersects the longitudinal axis 101 of the cannula 100 at a non-orthogonal angle α. Thus opening 134 in FIG. 2, which is illustrated relative to longitudinal axis 101 and transverse axis 102 of cannula 100, is slightly skewed relative to transverse axis 102, as are all other openings 130 in the plurality of openings 124.

The inventors have determined that various parameters of the pattern of openings 124 can be manipulated to achieve a desired stiffness in the cannula 100 along an axial portion of the cannula 100. For example, the distance between revolutions of the spiral, illustrated in FIG. 2 as the gap 136 between openings 130 in immediately adjacent revolutions of the spiral, can be increased or decreased to achieve a desired number of revolutions of the spiral per unit of length of the cannula 100, which, in turn, increases or decreases, respectively, the stiffness of the cannula along the axial portion containing the pattern of openings 124. Also, the distance between openings within a revolution of the spiral, illustrated in FIG. 2 as the gap 138 between openings, can be increased or decreased to achieve a desired number of openings in a revolution of the spiral. The major length 140 of the oblong rectangle formed by the openings 130 can be varied as well. Also, the ratio of the major length 140 of the oblong rectangle of the opening to the distance between openings within a revolution of the spiral, i.e., gap 138, can be increased or decreased to achieve a desired number of openings in a revolution of the spiral, which, in turn, increases or decreases, respectively, the stiffness of the cannula along the axial portion containing the pattern of openings 124. The kerf of the slits can also be increased or decreased to achieve a desired flexibility by choosing an appropriate angle α for the intersection of the planes containing the major axis m of individual openings 130 with the longitudinal axis 101 of the cannula 100.

A skilled artisan will be able to manipulate one or more of these parameters in a cannula according to a particular embodiment to achieve a desired flexibility along the axial portion containing a pattern of openings. Surprisingly, the inventors have determined that a cannula made in this manner retains enough stiffness to effectively serve as the innermost member of a delivery system useful for placing an intraluminal medical device at a point of treatment within a body vessel. While providing a desired degree of local flexibility through manipulation of the parameters described above, such a cannula is able to carry the intraluminal medical device of the delivery system, such as a stent, valve, filter or other expandable intraluminal medical device, and, effectively, serve as a pusher that provides the pushability and/or trackability needed for navigation of the delivery system to an intraluminal point of treatment.

Figures 4A, 4B, 4C:
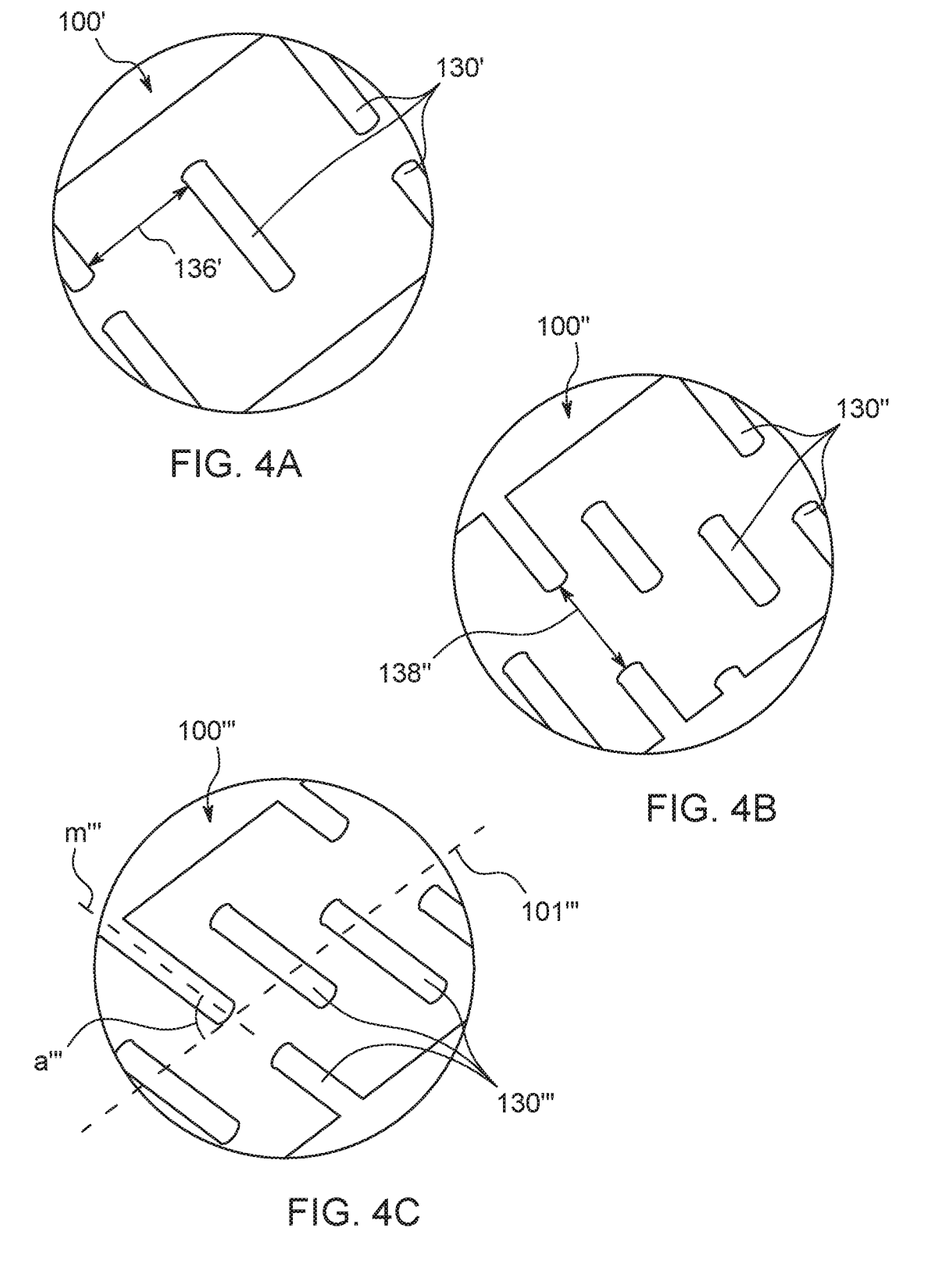
FIG. 4A is a magnified view of a portion of an alternative cannula.
FIG. 4B is a magnified view of a portion of another alternative cannula.
FIG. 4C is a magnified view of a portion of another alternative cannula.

Each of FIGS. 4A, 4B, and 4C illustrates an alternative cannula with wall openings arranged in an alternative pattern achieved by manipulating one or more of the parameters described above. In the cannula 100' illustrated in FIG. 4A, the gap 136' between openings 130' in immediately adjacent revolutions of the spiral is larger than the gap 136 used in cannula 100 illustrated in FIGS. 1 through 3.

The gap between openings in immediately adjacent revolutions of the spiral in a cannula according to a particular embodiment can have any suitable length as measured along the longitudinal axis of the cannula. A skilled artisan will be able to select an appropriate length for this gap for a particular cannula according to various considerations, including the nature of the material from which the cannula is formed and any desired flexibility in the axial length of the cannula along which the pattern of openings that contains the gaps extends. The inventors have determined that a gap the is between about 0.5 and about 40.0 times the axial width of the openings in the pattern of openings is suitable for a cannula intended to be used in an intraluminal medical device delivery system as described herein. The inventors also consider a gap that is between about 1 and about 5 times the axial width of the openings in the pattern of openings to be suitable for a cannula intended to be used in an intraluminal medical device delivery system as described herein. The inventors also consider a gap that is between about 1.5 and about 2.5 times the axial width of the openings in the pattern of openings to be suitable for a cannula intended to be used in an intraluminal medical device delivery system as described herein. The inventors also consider a gap that is about 2 times the axial width of the openings in the pattern of openings to be suitable for a cannula intended to be used in an intraluminal medical device delivery system as described herein.

In the cannula 100″ illustrated in FIG. 4B, the gap 138″ between openings 130″ within a revolution of the spiral is larger than the gap 138 used in cannula 100 illustrated in FIGS. 1 through 3.

The gap between openings within a revolution of the spiral in a cannula according to a particular embodiment can have any suitable length as measured along the major axis of the openings of revolution. A skilled artisan will be able to select an appropriate length for this gap for a particular cannula according to various considerations, including the nature of the material from which the cannula is formed and any desired flexibility in the axial length of the cannula along which the pattern of openings that contains the gaps extends. The inventors have determined that a gap that is between about 0.1 and about 2 times the axial length of the openings in the pattern of openings is suitable for a cannula intended to be used in an intraluminal medical device delivery system as described herein. The inventors consider a gap that is between about 0.25 and about 1.5 times the axial length of the openings in the pattern of openings to be suitable for a cannula intended to be used in an intraluminal medical device delivery system as described herein. The inventors also consider a gap that is between about 0.5 and about 1.25 times the axial length of the openings in the pattern of openings to be suitable for a cannula intended to be used in an intraluminal medical device delivery system as described herein. The inventors also consider a gap that is about 0.5 times the axial length of the openings in the pattern of openings to be suitable for a cannula intended to be used in an intraluminal medical device delivery system as described herein.

In the cannula 100′ illustrated in FIG. 4C, the kerf of the openings 130‴ is larger than the kerf used in cannula 100 illustrated in FIGS. 1 through 3. This is achieved structurally by using an angle $\alpha'''$ at which each of the planes containing a major axis of an opening 130‴ intersects the longitudinal axis 100′ of the cannula 100‴ that is smaller, or more acute, than the angle $\alpha$ used in cannula 100 illustrated in FIGS. 1 through 3.

The angle at which each of the planes containing a major axis of an opening intersects the longitudinal axis of a cannula according to a particular embodiment can have any suitable measure. A skilled artisan will be able to select an appropriate measure for this angle for a particular cannula according to various considerations, including the nature of the material from which the cannula is formed and any desired flexibility in the axial length of the cannula along which the pattern of openings that contains the angle extends. The inventors have determined that an angle that is between about 5 degrees and about 89 degrees is suitable for a cannula intended to be used in an intraluminal medical device delivery system as described herein. The inventors consider an angle that is between about 45 degrees and about 89 degrees to be suitable for a cannula intended to be used in an intraluminal medical device delivery system as described herein. The inventors also consider an angle that is between about 75 degrees and about 89 degrees to be suitable for a cannula intended to be used in an intraluminal medical device delivery system as described herein. The inventors also consider an angle that is about 85 degrees to be suitable for a cannula intended to be used in an intraluminal medical device delivery system as described herein. Also, it is noted that the angle can be disposed in either direction relative to the cannula. As a result, the openings in the pattern of openings in a cannula according to a particular embodiment can extend toward the proximal end of the cannula or toward the distal end of the cannula.

In the first example cannula 100, the pattern of openings 124 is uniform in that the various parameters described above—the distance between revolutions of the spiral, i.e., gap 136, the distance between openings within a revolution of the spiral, i.e., gap 138, the major length 140 of the oblong rectangle formed by the openings 130, the ratio of the major length 140 of the oblong rectangle of the openings 130 to the distance between openings within a revolution of the spiral, i.e., gap 138, and the kerf of the openings 130—are uniform throughout the pattern of openings 124. That is, the each of the parameters has a substantially constant value that does not vary within the axial portion of the cannula along which the pattern of openings 124 extends. For some cannula, though, it may be desirable to have one or more of these parameters vary within the axial portion of the cannula along which the pattern of openings 124 extends.

Figure 5:
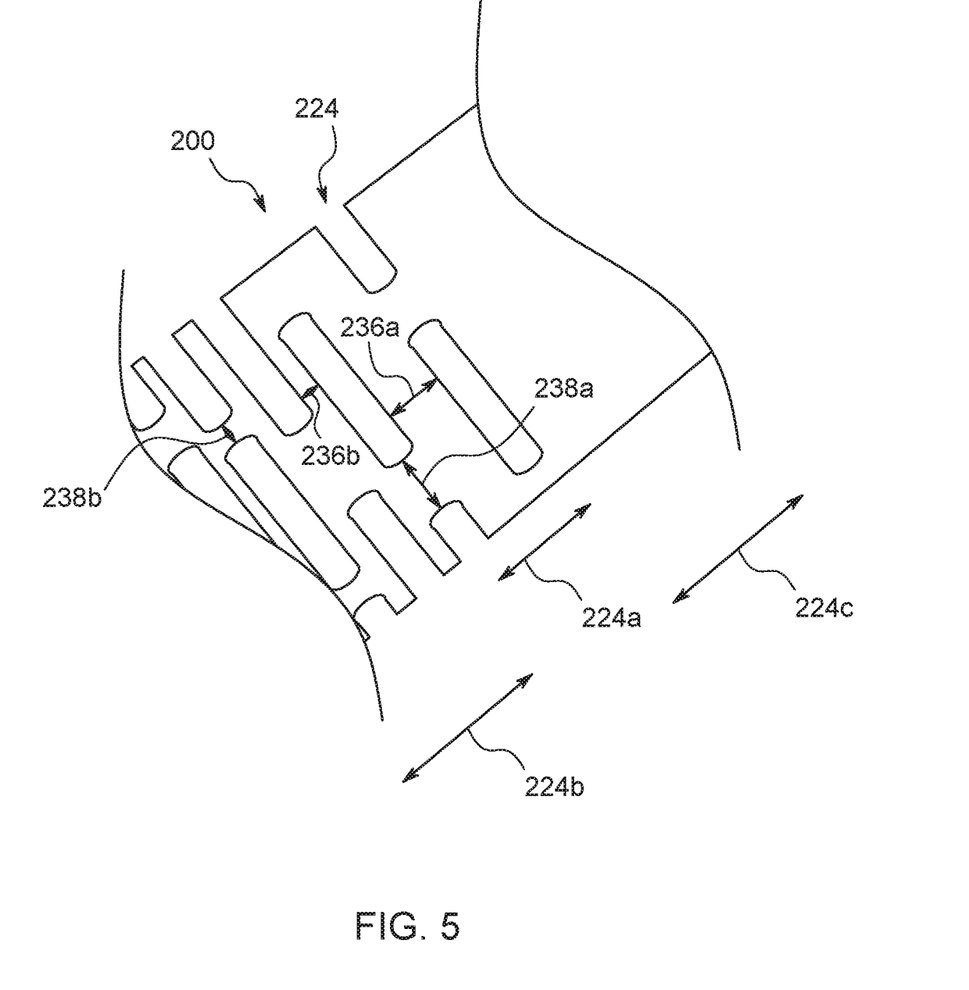
FIG. 5 is a magnified view of a portion of another example cannula.

FIG. 5 illustrates an example cannula 200 in which some of these parameters vary within the axial portion of the cannula 200 along which the pattern of openings 224 extends. For example, an intermediate portion 224a of the pattern of openings includes a first distance between revolutions of the spiral, i.e., gap 236a, and a first distance between openings within a revolution of the spiral, i.e., gap 238a. A proximal portion 224b of the pattern of openings includes a second distance between revolutions of the spiral, i.e., gap 236b, and a second distance between openings within a revolution of the spiral, i.e., gap 238b. Gap 236b is shorter in length that gap 236a. Similarly, gap 238b is shorter in length that gap 238a. A distal portion 224c of the cannula 200 is free of the pattern of openings 224. This construction, where one or more of the parameters described above is varied within a single plurality of openings along an axial portion of a cannula, can be advantageously used in a cannula according to a particular example to provide a stiffness transition between an axial portion of relatively low stiffness, such as proximal portion 224b in cannula 200, to an axial portion of the cannula of relatively high stiffness, such as distal portion 224c of cannula 200, along which the pattern of openings 224 does not extend.

While the pattern of openings can extend along the entire axial length of a cannula, such as in the first example cannula 100, a pattern of openings can extend along any suitable axial length of a cannula according to a particular embodiment. A skilled artisan will be able to select an appropriate axial length for a pattern of openings in a cannula according to a particular embodiment based on various considerations, including whether it is desirable to include any axial portions of the cannula that have a localized stiffness that is greater than the stiffness of the axial portions along which the pattern of openings extends. Each of FIGS. 6, 7, and 8 illustrates a cannula having a pattern of openings that extends along only a portion, or portions, of the entire axial length of the example cannula.

Figure 6:
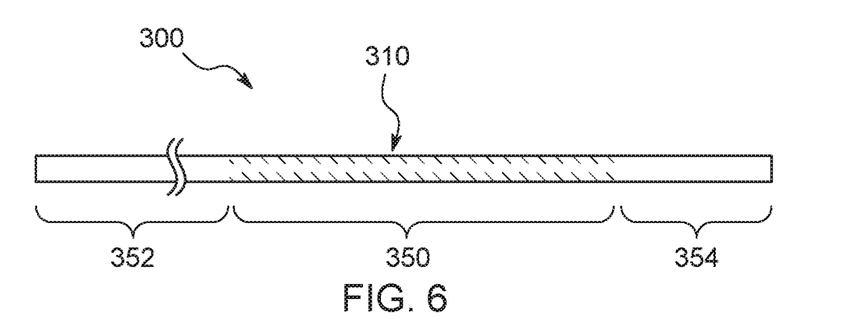
FIG. 6 is a side view, partially broken away, of another example cannula.

The cannula 300 illustrated in FIG. 6 has a pattern of openings 310 that extends along an intermediate portion 350 of the axial length of the cannula 300. The pattern of openings 310 can be any suitable pattern of openings according to an embodiment, including those described above. The intermediate portion 350 extends between a proximal portion 352 and a distal portion 354, each of which is free of the pattern of openings 310 and, indeed, comprises a solid, non-interrupted circumferential wall. This structural configuration is considered advantageous at least because it provides a relatively stiff distal portion 354 that is suitable for carrying an intraluminal medical device when the cannula 300 is included as a component in a delivery system, such as those described below. Furthermore, this configuration provides a relatively stiff proximal portion 352 that facilitates manipulation of the cannula 300, or a delivery system that includes the cannula, by a user.

Each of the intermediate 350, proximal 352 and distal 354 portions can extend along any suitable axial length of the cannula 300, and a skilled artisan will be able to determine suitable axial lengths for each portion in a particular cannula based on various considerations, including the axial length of any intraluminal medical device with which the cannula is intended to be used. Furthermore, the portions can have any suitable relative axial lengths. For example, in the illustrated embodiment, the proximal portion 352 is longer than the distal portion 354. It is noted, though, that an opposite relationship could be used, i.e., the distal portion of a cannula can have a longer axial length than a proximal portion.

Figure 7:
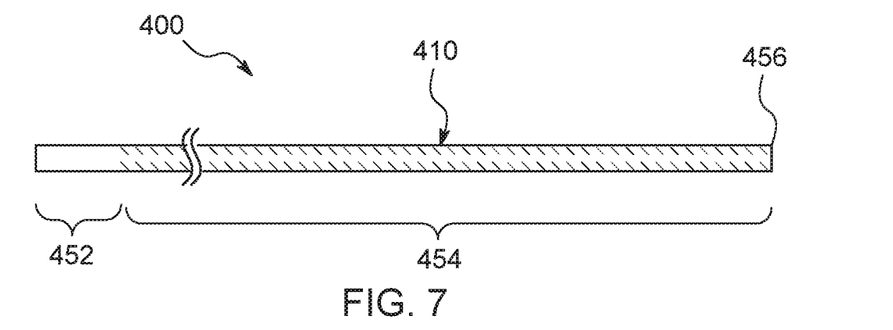
FIG. 7 is a side view, partially broken away, of another example cannula.
Figure 8:
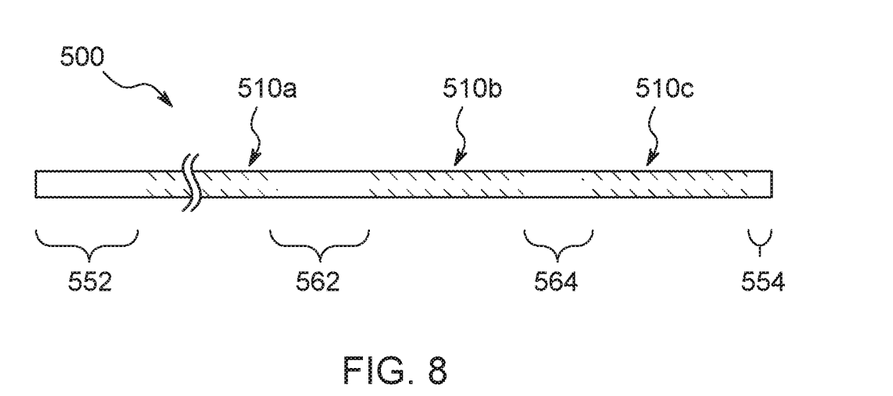
FIG. 8 is a side view, partially broken away, of another example cannula.

The cannula 400 illustrated in FIG. 7 has a pattern of openings 410 that extends along a distal portion 454 of the axial length of the cannula 400. The pattern of openings 410 can be any suitable pattern of openings according to an embodiment, including those described above. The distal portion 454 includes the distal end 456 of the cannula 400. A proximal portion 452 is free of the pattern of openings 410 and, indeed, comprises a solid, non-interrupted circumferential wall. This structural configuration is considered advantageous at least because it provides a relatively flexible distal portion 454 that is suitable for carrying some intraluminal medical devices through tortuous anatomy, such as neurovascular stents. Furthermore, this configuration provides a relatively stiff proximal portion 452 that facilitates manipulation of the cannula 400, or a delivery system that includes the cannula, by a user.

Each of the proximal 452 and distal 454 portions can extend along any suitable axial length of the cannula 400, and a skilled artisan will be able to determine suitable axial lengths for each portion in a particular cannula based on various considerations, including the axial length of any intraluminal medical device with which the cannula is intended to be used. Furthermore, the portions can have any suitable relative axial lengths. For example, in the illustrated embodiment, the proximal portion 452 is shorter than the distal portion 454. It is noted, though, that an opposite relationship could be used, i.e., the distal portion of a cannula can have a longer axial length than a proximal portion.

The cannula 500 illustrated in FIG. 8 has a pattern of openings 510 that comprises distinct sections 510a, 510b, and 510c that are separated from each other by intervening sections 562, 564. The cannula 500 also includes a proximal portion 552 and a distal portion 554, each of which is free of the pattern of openings 510 and, indeed, comprises a solid, non-interrupted circumferential wall. In each of the distinct sections 510a, 510b, 510c, the pattern of openings 510 can be any suitable pattern of openings according to an embodiment, including those described above. Furthermore, the pattern of openings in each of the distinct sections 510a, 510b, 510c can be the same pattern as in the other distinct sections 510a, 510b, 510c. Alternatively, the pattern of openings in each of the distinct sections 510a, 510b, 510c can be different from the pattern of openings in one or two of the other distinct sections 510a, 510b, 510c. Also, each of the distinct sections 510a, 510b, 510c can have any suitable axial length along the cannula 500. In the illustrated embodiment, each of the distinct sections 510a, 510b, 510c extends along an axial length of the cannula 500 that is the same as the axial length along which the other of the distinct sections 510a, 510b, 510c extends along. It is noted, though, that each of the distinct sections 510a, 510b, 510c can extend along an axial length that id different from the axial length along which one or more of the other distinct sections 510a, 510b, 510c extends along. Also, in any given embodiment, any suitable number of distinct sections can be used.

A cannula according to an example can be made of any suitable material. A skilled artisan will be able to select an appropriate material for a cannula according to a particular example based on various considerations, including any desired overall stiffness and/or flexibility of the cannula and the point of treatment at which the cannula is intended to be used. Metals are considered advantageous for the examples described and illustrated herein, but polymeric, including plastic materials currently considered suitable for use in medical devices, and other materials can be used. Stainless steel is considered particularly advantageous for the example cannulae described and illustrated herein at least because of its well-characterized nature, acceptance as a material used in medical devices temporarily placed within body lumens, and ready availability. Examples of other metals considered suitable for use in cannulae according to particular examples include cobalt-chrome and shape memory alloys, such as nickel-titanium alloys. Examples of polymeric materials considered suitable for use in cannulae according to particular examples include polyamide materials, such as nylon, and other polymeric materials. A cannula can include multiple materials, too, if desired. For example, an axial length of one material can be joined to an axial length of another material to create a cannula. The pattern of openings in such a cannula can be disposed on any suitable axial portion of the cannula, such as an axial portion comprising only the first material, an axial portion comprising only the second material, or an axial portion comprising both the first and the second material.

It is noted that a cannula according to a particular example can have a lumen of any suitable diameter and that the dimensions of the lumen of the cannulae described and illustrated herein are illustrative only. A skilled artisan will be able to select an appropriate lumen size for a cannula according to a particular example based on various considerations, including the dimensions of the lumen of the body vessel within which the cannula and/or delivery system is intended to be used.

It is noted that a cannula according to a particular example can have a circumferential wall of any suitable wall thickness and that the wall thicknesses of the circumferential wall of the cannulae described and illustrated herein are illustrative only. A skilled artisan will be able to select an appropriate wall thickness for a cannula according to a particular embodiment based on various considerations, including any desired overall stiffness of the cannula. Indeed, the inventors have determined that a wall thickness can be selected when making a cannula according to a particular example that provides a desired stiffness to any axial portions of the cannula not having a pattern of openings disposed on the portion of the circumferential wall within that particular axial portion. As described in detail below, combining a selected wall thickness with one or more selected patterns of openings along the axial length of a cannula allows a user to make a cannula with desired global and local stiffnesses.

The cannulae can be used as a component of a delivery system useful for delivering an intraluminal medical device to a point of treatment within a lumen of a body vessel. The desirable stiffness properties of the cannulae provide delivery systems that are particularly well suited for delivering intraluminal medical devices to points of treatment within relatively small body vessels. For example, delivery systems that includes example cannulae are expected to be well-suited for delivery of prosthetic venous valves, neurovascular stents and other intraluminal medical devices.

Figure 9:
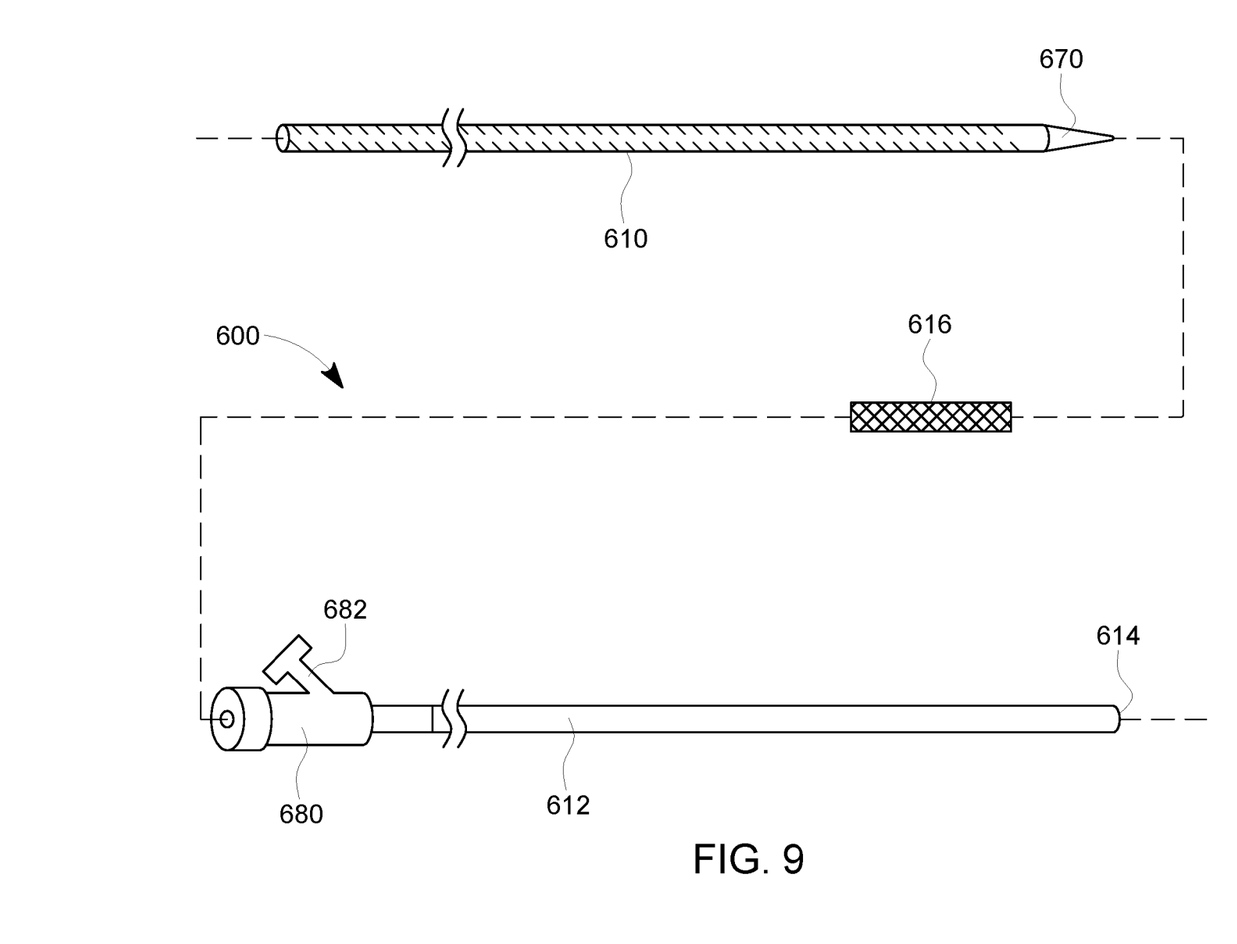
FIG. 9 is an exploded view of an example delivery system.

FIG. 9 illustrates a first example delivery system 600. The delivery system 600 includes a cannula 610 according to an embodiment disposed within the lumen 614 defined by an outer tubular member 612. An intraluminal medical device 616 is circumferentially disposed around the cannula 610 and within the lumen 614 of the outer tubular member 612.

The cannula 610 can comprise any suitable cannula according to an embodiment and a skilled artisan will be able to select a suitable cannula for inclusion in a particular delivery system based on various considerations, including the nature, size and configuration of the intraluminal medical device 614 and any desired local and/or global flexibility and/or stiffness properties for the delivery system. In the illustrated delivery system 610, a cannula having a pattern of openings 620 that extends along the entire axial length of the cannula 610 is included in the delivery system 600. This is considered particularly advantageous for delivery systems for which overall flexibility is the primary desired characteristic.

The intraluminal medical device 616 can comprise any suitable intraluminal medical device. The delivery systems are particularly well-suited, however, for use with self-expandable medical devices, including stents, valves, such as venous valve and cardiac valves, filters, occluders, and other intraluminal medical devices.

Additional components can be attached to the cannula 610 using conventional approaches. For example, in the illustrated embodiment, a conical distal tip 670 has been disposed on and secured to the distal end of the cannula 610. Similarly, additional components can be attached to the elongate tubular member 614 using conventional approaches. For example, in the illustrated embodiment, a hub 680 providing a side-arm connector 682 is disposed on and secured to the proximal end of the elongate tubular member 612.

It is noted that the cannula 610 provides desirable flexibility and pushability characteristics for the delivery system 600 such that additional components, such as a pusher, are not required for its use. Thus, the delivery system can consist only of a cannula according to an embodiment, such as cannula 610, an elongate tubular member 612, and an intraluminal medical device 616. If desired or necessary, a wireguide (not shown) can be used with the delivery system for conventional navigation purposes.

Figure 10:
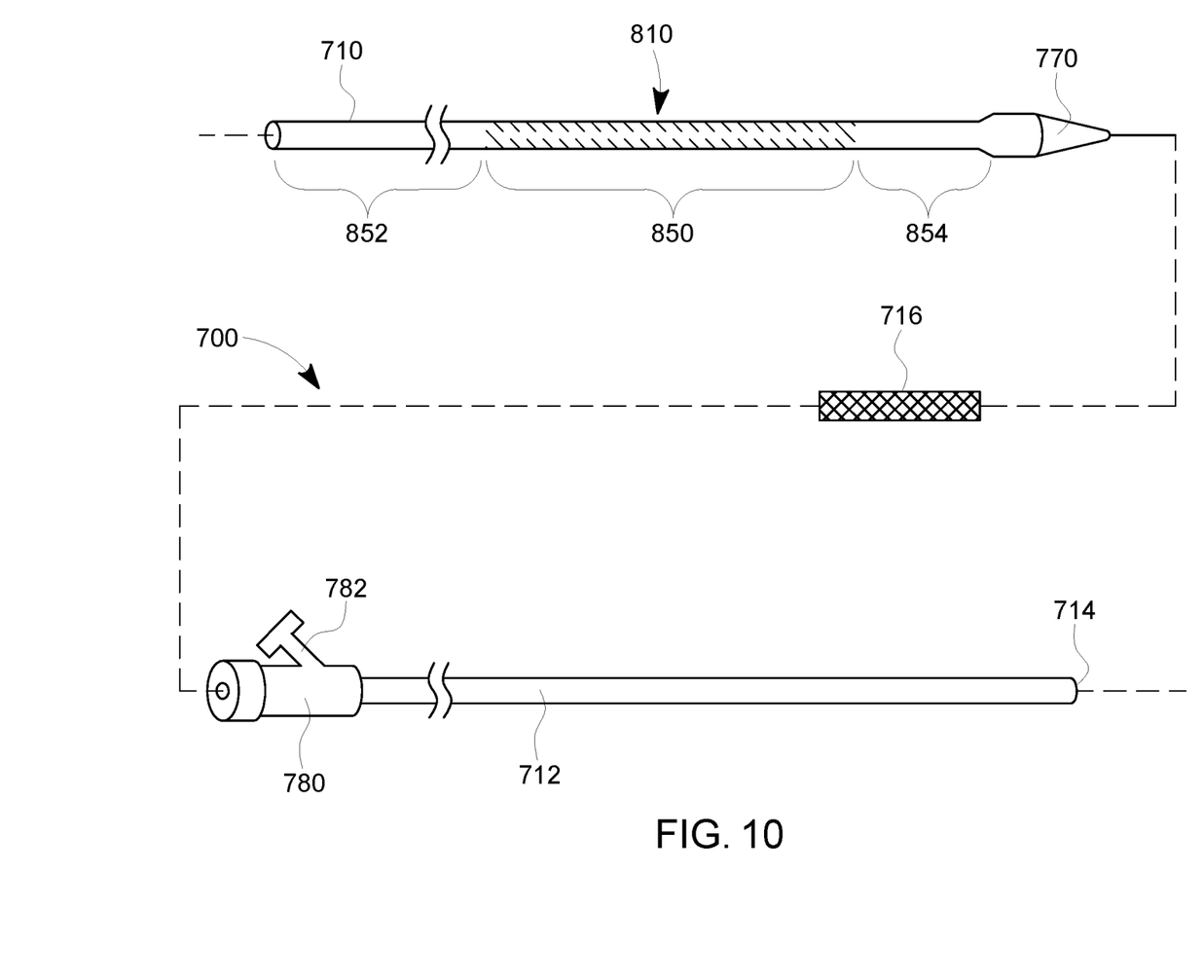
FIG. 10 is an exploded view of another example delivery system.

FIG. 10 illustrates a second example delivery system 700. Delivery system 700 is similar to delivery system 600 described above and illustrated in FIG. 9, except as detailed below. Thus, delivery system 700 includes a cannula 710 according to an embodiment disposed within the lumen 714 defined by an outer tubular member 712. An intraluminal medical device 716 is circumferentially disposed around the cannula 710 and within the lumen 714 of the outer tubular member 712. An elongate double-tapered distal tip 770 has been disposed on and secured to the distal end of the cannula 710. A hub 780 providing a side-arm connector 782 is disposed on and secured to the proximal end of the elongate tubular member 712.

In this embodiment, the cannula 710 is similar to the cannula 300 illustrated in FIG. 6. Thus, the cannula 710 has a pattern of openings 810 that extends along an intermediate portion 850 of the axial length of the cannula 710. The pattern of openings 810 can be any suitable pattern of openings according to an embodiment, including those described above. The intermediate portion 850 extends between a proximal portion 852 and a distal portion 854, each of which is free of the pattern of openings 810 and, indeed, comprises a solid, non-interrupted circumferential wall. This structural configuration is considered advantageous at least because it provides a relatively stiff distal portion 854 that is suitable for carrying the intraluminal medical device 716 and provides a relatively stiff proximal portion 852 that facilitates manipulation of the delivery system 700 during use.

Figure 11:
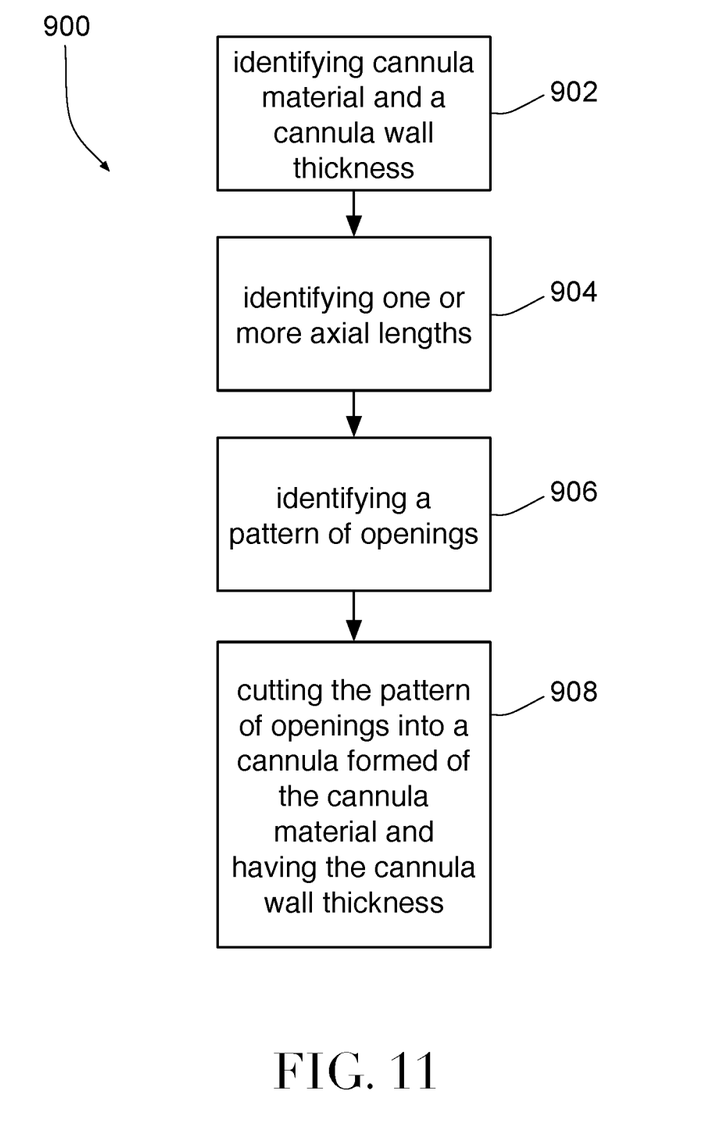
FIG. 11 is a flowchart representation of an example method of making a cannula.

FIG. 11 illustrates an example method 900 of making a cannula. A first step 902 comprises identifying a cannula material and a cannula wall thickness that provides a desired global stiffness for said cannula. Another step 904 comprises identifying one or more axial lengths of said cannula along which a localized stiffness, different from the desired global stiffness, is desired. Another step 906 comprises identifying a pattern of openings that will provide the desired localized stiffness when cut into a cannula formed of the cannula material and having the cannula wall thickness. Another step 908 comprises cutting the pattern of openings into a cannula formed of the cannula material and having the cannula wall thickness at axial positions that correspond to the one or more axial lengths. This step 908 can be performed using any suitable technique and/or process, such as laser cutting followed by post-processing to remove any slag created as a result of the cutting. Alternatively, a suitable laser capable of cutting the pattern of openings entirely by vaporization can be used to avoid the need for removal of slag in post-processing.

Figure 12:
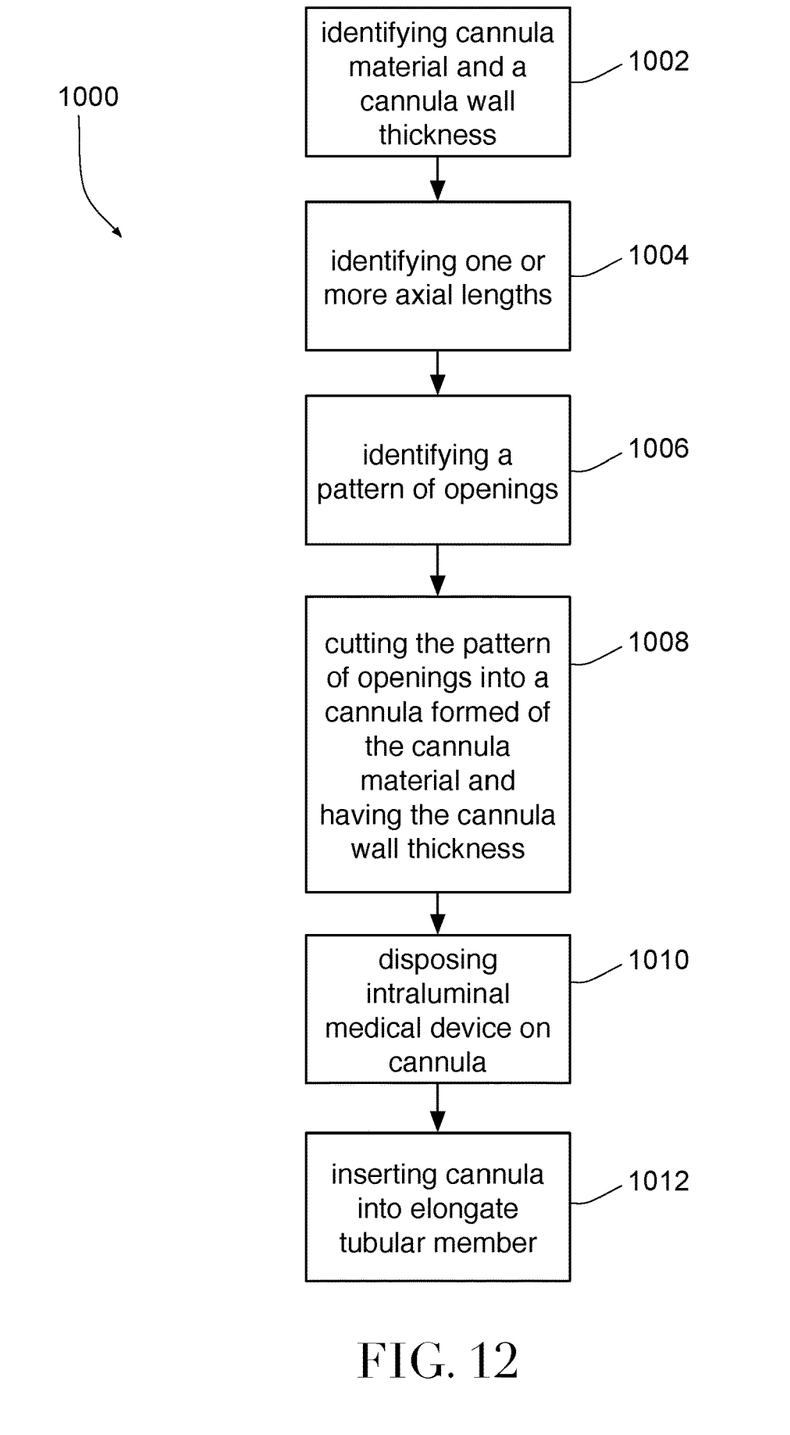
FIG. 12 is a flowchart representation of an example method of making a delivery system.

FIG. 12 illustrates an example method 1000 of making a delivery system. A first step 1002 comprises identifying a cannula material and a cannula wall thickness that provides a desired global stiffness for said cannula. Another step 1004 comprises identifying one or more axial lengths of said cannula along which a localized stiffness, different from the desired global stiffness, is desired. Another step 1006 comprises identifying a pattern of openings that will provide the desired localized stiffness when cut into a cannula formed of the cannula material and having the cannula wall thickness. Another step 1008 comprises cutting the pattern of openings into a cannula formed of the cannula material and having the cannula wall thickness at axial positions that correspond to the one or more axial lengths. Another step 1010 comprises disposing an intraluminal medical device on a portion of the cannula that is free of the pattern of openings. Another step 1012 comprises inserting the cannula into an elongate tubular member defining a lumen such that the intraluminal medical device is circumferentially disposed about the cannula and within the lumen.

While the examples described above reference specific features of particular drawings, it is understood that the various elements and/or features described herein in connection with one particular embodiment can be combined with those of another without departing from the scope of the invention. Furthermore, the cannulae, delivery systems and methods described and illustrated herein are examples. As such, they are not intended to limit the scope of protection sought in any manner. Rather, they serve only to aid those skilled in the art to make apparatuses and to practice methods in accordance with the invention.

We claim:

1. A delivery system, comprising:
   a cannula, comprising:
      an elongate tubular member having a lengthwise axis and a circumferential wall extending between a proximal end and a distal end and defining an interior lumen;
      the elongate tubular member having an intermediate axial portion extending between a proximal axial portion that includes the proximal end and a distal axial portion that includes the distal end; and
      a pattern of openings in the circumferential wall of the elongate tubular member, the pattern of openings comprising a plurality of openings arranged in an interrupted spiral that extends circumferentially along the intermediate axial portion of the elongate tubular member, the pattern of openings comprising distinct sections separated from each other by intervening sections, the intervening sections free of the pattern of openings and comprising an uninterrupted circumferential wall;
      wherein the proximal axial portion and the distal axial portion are free of the pattern of openings and comprise an uninterrupted circumferential wall; and
      wherein the proximal portion is longer than the distal portion;
   an intraluminal medical device disposed on the distal axial portion of the elongate tubular member; and
   an elongate outer tubular member defining an outer tubular member lumen;
   wherein the cannula is disposed within the outer tubular member lumen such that the intraluminal medical device is circumferentially disposed about the cannula and within the outer tubular member lumen.

2. The delivery system of claim 1, wherein each opening of the plurality of openings comprises an elongate slit that extends through the entire thickness of the circumferential wall of the elongate tubular member.

3. The delivery system of claim 1, wherein a portion of the circumferential wall is disposed between openings in immediately adjacent revolutions of the interrupted spiral; and
   wherein each opening of the plurality of openings has an axial width;
   wherein the portion has a length along the lengthwise axis of the elongate tubular member that is between about 0.5 times and about 40 times the axial width of the openings in the immediately adjacent revolutions of the interrupted spiral.

4. The delivery system of claim 1, wherein portions of the circumferential wall are disposed between immediately adjacent revolutions of the interrupted spiral; and
   wherein the portions have uniform lengths along the lengthwise axis of the elongate tubular member.

5. The delivery system of claim 1, wherein portions of the circumferential wall are disposed between immediately adjacent revolutions of the interrupted spiral; and
   wherein the portions have varying lengths along the lengthwise axis of the elongate tubular member.

6. The delivery system of claim 1, wherein a portion of the circumferential wall is disposed between immediately adjacent openings within a revolution of the interrupted spiral; and
   wherein each opening of the plurality of openings has an axial width;
   wherein the portion has a circumferential length along the elongate tubular member that is between about 0.1 times and about 2 times the axial width of the immediately adjacent openings within a revolution of the interrupted spiral.

7. The delivery system of claim 1, wherein portions of the circumferential wall are disposed between immediately adjacent openings within a revolution of the interrupted spiral; and
   wherein the portions have uniform circumferential lengths along the elongate tubular member.

8. The delivery system of claim 1, wherein portions of the circumferential wall are disposed between immediately adjacent openings within a revolution of the interrupted spiral; and
   wherein the portions have varying circumferential lengths along the elongate tubular member.

9. The delivery system of claim 1, further comprising a double-tapered distal tip secured to the distal end of the elongate tubular member;
   wherein the double-tapered distal tip has an outer diameter that is greater than an outer diameter of the elongate tubular member.

10. The delivery system of claim 1, wherein the elongate tubular member comprises a metal.

11. A delivery system, comprising:
    a cannula, comprising:
       an elongate tubular member having a lengthwise axis and a circumferential wall extending between a proximal end and a distal end and defining an interior lumen;
       a double-tapered distal tip secured to the distal end of the elongate tubular member and having an outer diameter that is greater than an outer diameter of the elongate tubular member;
       the elongate tubular member having an intermediate axial portion extending between a proximal axial portion that includes the proximal end and a distal axial portion that includes the distal end; and
       a pattern of openings in the circumferential wall of the elongate tubular member, the pattern of openings comprising a plurality of openings arranged in an interrupted spiral that extends circumferentially along the intermediate axial portion of the elongate tubular member;

wherein the proximal axial portion and the distal axial portion are free of the pattern of openings and comprise an uninterrupted circumferential wall; and wherein the proximal portion is longer than the distal portion;

an intraluminal medical device disposed on the distal axial portion of the elongate tubular member; and an elongate outer tubular member defining an outer tubular member lumen;

wherein the cannula is disposed within the outer tubular member lumen such that the intraluminal medical device is circumferentially disposed about the cannula and within the outer tubular member lumen.

12. The delivery system of claim 11, wherein each opening of the plurality of openings comprises an elongate slit that extends through the entire thickness of the circumferential wall of the elongate tubular member.

13. The delivery system of claim 11, wherein a portion of the circumferential wall is disposed between openings in immediately adjacent revolutions of the interrupted spiral; and wherein each opening of the plurality of openings has an axial width;

wherein the portion has a length along the lengthwise axis of the elongate tubular member that is between about 0.5 times and about 40 times the axial width of the openings in the immediately adjacent revolutions of the interrupted spiral.

14. The delivery system of claim 11, wherein portions of the circumferential wall are disposed between immediately adjacent revolutions of the interrupted spiral; and wherein the portions have uniform lengths along the lengthwise axis of the elongate tubular member.

15. The delivery system of claim 11, wherein portions of the circumferential wall are disposed between immediately adjacent revolutions of the interrupted spiral; and wherein the portions have varying lengths along the lengthwise axis of the elongate tubular member.

16. The delivery system of claim 11, wherein a portion of the circumferential wall is disposed between immediately adjacent openings within a revolution of the interrupted spiral; and wherein each opening of the plurality of openings has an axial width;

wherein the portion has a circumferential length along the elongate tubular member that is between about 0.1 times and about 2 times the axial width of the immediately adjacent openings within a revolution of the interrupted spiral.

17. The delivery system of claim 11, wherein portions of the circumferential wall are disposed between immediately adjacent openings within a revolution of the interrupted spiral; and wherein the portions have uniform circumferential lengths along the elongate tubular member.

18. The delivery system of claim 11, wherein portions of the circumferential wall are disposed between immediately adjacent openings within a revolution of the interrupted spiral; and wherein the portions have varying circumferential lengths along the elongate tubular member.

19. The delivery system of claim 11, wherein the elongate tubular member comprises a metal.

20. The delivery system of claim 19, wherein the metal comprises stainless steel.

* * * * *